(12) United States Patent
Porat

(10) Patent No.: US 9,220,863 B2
(45) Date of Patent: Dec. 29, 2015

(54) KINK-RESISTANT GAS DELIVERY TUBE

(75) Inventor: Ron Porat, D.N. Haela (IL)

(73) Assignee: Oridion Medical 1987 Ltd., Jerusalem (IL)

(*) Notice: Subject to any disclaimer, the term of this patent is extended or adjusted under 35 U.S.C. 154(b) by 336 days.

(21) Appl. No.: 13/991,815

(22) PCT Filed: Dec. 7, 2011

(86) PCT No.: PCT/IL2011/050046
§ 371 (c)(1),
(2), (4) Date: Jun. 5, 2013

(87) PCT Pub. No.: WO2012/077114
PCT Pub. Date: Jun. 14, 2012

(65) Prior Publication Data
US 2013/0247904 A1    Sep. 26, 2013

Related U.S. Application Data

(60) Provisional application No. 61/421,233, filed on Dec. 9, 2010.

(51) Int. Cl.
*A61M 16/08* (2006.01)
*A61M 25/14* (2006.01)
*A61M 25/00* (2006.01)
*A61M 39/08* (2006.01)

(52) U.S. Cl.
CPC ....... *A61M 16/0875* (2013.01); *A61M 25/0023* (2013.01); *A61M 39/08* (2013.01); *A61M 2025/0059* (2013.01)

(58) Field of Classification Search
CPC .......... A61M 25/005; A61M 25/0023; A61M 25/0032; A61M 2025/0059; A61M 39/08; A61M 16/0875; A61M 16/08; A61M 16/0666
USPC ........................................... 138/108, 153, 159
See application file for complete search history.

(56) References Cited

U.S. PATENT DOCUMENTS

| | | | |
|---|---|---|---|
| 1,596,754 A * | 8/1926 | Moschelle | 604/541 |
| 3,720,235 A | 3/1973 | Schrock | |
| 4,840,623 A | 6/1989 | Quackenbush | |
| 5,682,925 A | 11/1997 | Seckel | |
| 5,797,882 A | 8/1998 | Purdy | |
| 6,679,298 B2 | 1/2004 | Espinasse | |
| 7,406,966 B2 * | 8/2008 | Wondka | 128/207.18 |
| 2003/0059213 A1* | 3/2003 | Mackie et al. | 392/480 |
| 2004/0194781 A1* | 10/2004 | Fukunaga et al. | 128/203.12 |
| 2005/0010169 A1* | 1/2005 | Kuhlein et al. | 604/93.01 |
| 2006/0161135 A1* | 7/2006 | VanDerWoude | 604/524 |
| 2009/0087606 A1* | 4/2009 | Julien | 428/36.7 |

OTHER PUBLICATIONS

Orr et al., (1985) Fabrication techniques for thin-walled, kink-resistant tubular structures for use in medical devices. Med Biol Eng Comput 23(1): 77-8.

* cited by examiner

*Primary Examiner* — Justine Yu
*Assistant Examiner* — Douglas Sul
(74) *Attorney, Agent, or Firm* — Rodney J. Fuller; Booth Udall Fuller, PLC

(57) ABSTRACT

A kink-resistant gas delivery tube configured to be directly connected to a circular male plug, the tube having an internal geometry of multiple concave and convex areas each having an apex, wherein an angle α between a tangent line to the apex of a concave area and a tangent line to a point of maximum slope between the apexes is 30 degrees or less, or wherein an angle β between a tangent line to the apex of a convex area and a tangent line to a point of maximum slope between the apexes is 30 degrees or less.

14 Claims, 3 Drawing Sheets

US 9,220,863 B2

KINK-RESISTANT GAS DELIVERY TUBE

RELATED APPLICATION DATA

This application is the U.S. National Stage of International Application No. PCT/IL2011/050046, filed Dec. 7, 2011, which claims the benefit of U.S. Provisional Application No. 61/421,233, filed Dec. 9, 2010, the contents of each of which are herein expressly incorporated by reference for all purposes.

FIELD OF THE INVENTION

An aspect of some embodiments relates to a kink-resistant gas delivery tube.

BACKGROUND OF THE INVENTION

Tubes, connectors, nipples and other types of equipment which are used in respiratory therapy are commonly subject to strict requirements, meant to ensure their suitability for medical use. Such equipment is often used for the supply of medicinal gasses, such as oxygen, to patients.

A number of standards, such as International Standard ISO 5356-1:2004, European Standard No. EN 13544-2:2002E, British Standard No. BS EN 13544-2:2002+A1:2009 (all three incorporated herein by reference in their entirety) and others, list numerous requirements which respiratory therapy equipment must comply with. One of the many requirements is kink-resistance. A tube used for the delivery of gas has to be highly reliable, to the degree it is still able to deliver at least some gas to the patient when folded, squashed or the like.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

There is provided, in accordance with an embodiment, a kink-resistant gas delivery tube configured to be directly connected to a circular male plug, the tube having an internal geometry of multiple concave and convex areas each having an apex, wherein an angle α between a tangent line to the apex of a concave area and a tangent line to a point of maximum slope between the apexes is 30 degrees or less, or wherein an angle β between a tangent line to the apex of a convex area and a tangent line to a point of maximum slope between the apexes is 30 degrees or less.

In some embodiments, angle α is in the range of approximately 5-15 degrees.

In some embodiments, angle α is in the range of approximately 16-29 degrees.

In some embodiments, angle β is in the range of approximately 5-15 degrees.

In some embodiments, angle β is in the range of approximately 16-29 degrees.

In some embodiments, a ratio between angle α and angle β is in the range of approximately 1:1 to 1:4.5.

In some embodiments, a ratio between angle β and angle α is in the range of approximately 1:1 to 1:4.5.

There is provided, in accordance with an embodiment, a kink-resistant gas delivery tube configured to be directly connected to a circular male plug, the tube having an internal geometry of multiple concave and convex areas, wherein a ratio between a wall thickness of said tube at a concave area and a convex area is in the range of 1:1.25 to 1:3.

In some embodiments, said tube has an outer diameter of approximately 6 millimeters and a wall thickness of approximately 0.4 millimeters at a concave area and 0.8 millimeters at a convex area.

In some embodiments, said tube is made of soft PVC.

In some embodiments, said tube has a flow resistance of less than approximately 0.25 kPa/meter at a flow rate of 4 liters per minute.

In some embodiments, said tube has a flow resistance of approximately 0.11 kPa/meter at a flow rate of 4 liters per minute.

In some embodiments, said tube has a flow resistance of between approximately 0.07 and 0.15 kPa/meter at a flow rate of 4 liters per minute.

In some embodiments, said tube, when kinked, enables a flow rate of approximately 7.5 liters per minute or more with a resistance less than approximately 0.25 kPa/meter.

In some embodiments, said tube, when kinked, enables a flow rate of approximately 10 liters per minute or more.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

An aspect of some embodiments relates to a gas delivery tube having a geometry and made from such material which advantageously cause it to be both kink-resistant and suitable for connection to a circular male plug. Such a tube may be especially beneficial in the delivery of a medicinal gas, commonly oxygen, to a patient.

Figure 1A:
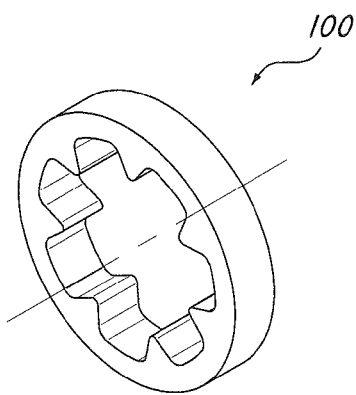
FIG. 1A shows a perspective view of a first exemplary tube geometry, according to the prior art.
Figure 1B:
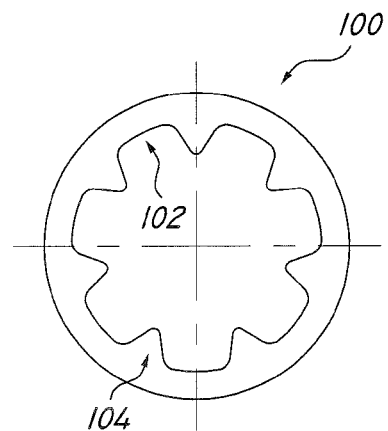
FIG. 1B shows a cross-sectional view of the first exemplary tube geometry, according to the prior art.

As described above, the need for the kink-resistance capability of gas delivery tubes stems mainly from the desire to supply gas to the patient in a highly reliable manner. FIGS. 1A-B and 2A-B show exemplary prior art kink-resistant tubes. Referring now to FIG. 1A, a tube 100 having what is often called a "star" geometry is shown in perspective. FIG. 1B shows a cross sectional view of the same tube 100, with its concavities 102 and convexities 104 more clearly visible. By virtue of this "star" geometry, when tube 100 is folded or when another external force is exerted on it, some space is still maintained between one or more opposing concavities 102 and/or convexities 104, allowing for passage of at least some of the gas.

Figure 2A:
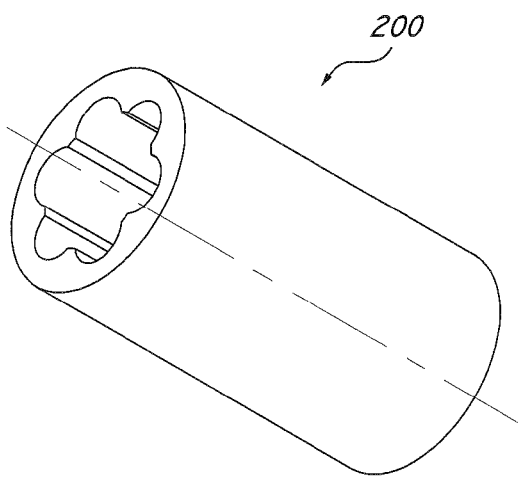
FIG. 2A shows a perspective view of a second exemplary tube geometry, according to the prior art.
Figure 2B:
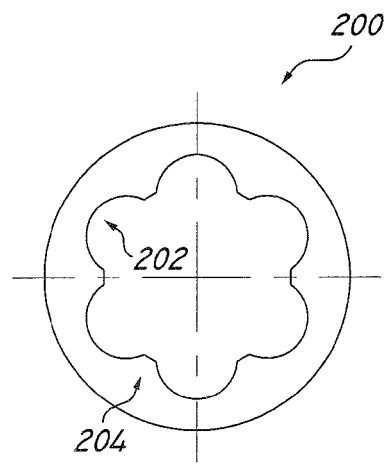
FIG. 2B shows a cross-sectional view of the second exemplary tube geometry, according to the prior art.

FIG. 2A shows another exemplary prior art kink-resistant tube 200. Tube 200, shown in perspective, demonstrates an additional kink-resistant geometry. In FIG. 2B, concavities 202 of tube 200 are essentially round, while convexities 204 are straight areas between the concavities.

Kink-resistant tubes, naturally, have to be connected to a gas source at one end, and to a patient interface (such as a mask, a nasal cannula and/or the like) at the other end. The connection to these features is often made using circular male plugs (or "nipples") that exist at the gas source and/or at the patient interface. However, the internal concavity-convexity geometry of prior art tubes often makes it inefficient to connect them directly to the gas source and the patient interface; this geometry does not provide for a gas-tight connection, since essentially only the convexities of the geometry are able to contact the circular male plug, and therefore gas can escape in the grooves formed between plug and the concavities. Hence, special adapters are usually used to mediate between the concave-convex tube and the gas source and/or the patient interface. Such adapters usually match the outer diameter of the tube geometry on one side, and have a circular geometry on the other side. They are commonly being glued to one or both ends of the tube.

Despite the fact that the adapters often provide a reasonable solution to the problem of connecting a tube, such as a kink-resistant tube, to gas supply and/or to a patient interface, this is not a sufficient solution for all scenarios. Many times, during the course of medical treatment of a patient, the gas delivery tube being used is determined to be too long. Then, the tube has to be discarded and replaced by a new, shorter one. It would be advantageous to provide a gas delivery tube which is both kink-resistant and configured to be directly and tightly connected to a male plug, so as to both eliminate the need for adapters and allow the tube to be efficiently shortened by way of cutting it (using scissors, for example) and re-connecting the new end to the patient interface or the gas supply nipple without producing a leak at the connector and risk to the patient.

Another scenario in which usage of a gas delivery tube which is both kink-resistant and configured to be directly and tightly connected to a male plug may be advantageous, is when a kink-resistant tube is connected, at the patient's end, to a low flow patient interface such as a nasal cannula (which commonly supplies up to approximately 5 liters per minute, but may nonetheless supply a higher or lower volume). Then, an urgent need might arise to significantly increase the oxygen supply, by switching to a facial mask adapted to deliver, typically, up to about 15 liters per minute, but may deliver a higher or a lower amount of gas per minute. The present, advantageous design may allow the caregiver to cut the tube close to the nasal cannula and connect it immediately to a face mask, without disconnecting the tube from the gas supply nipple of the regulator.

Figure 3:
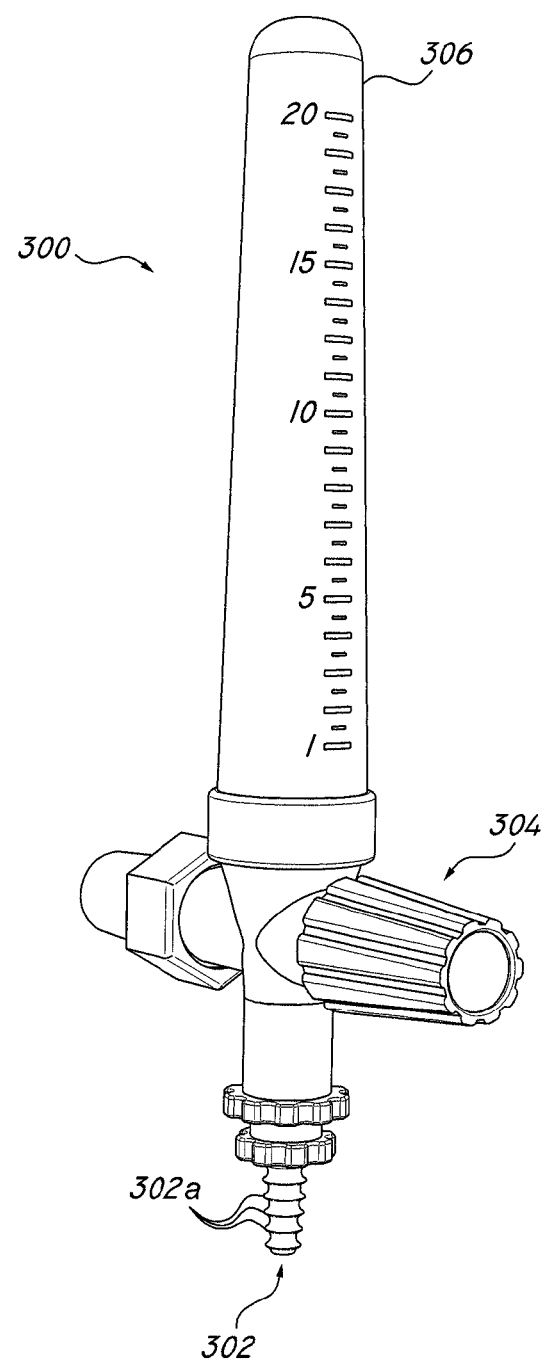
FIG. 3 shows a semi-pictorial view of a gas regulator, according to the prior art.

Reference is now made to FIG. 3, which shows a semi-pictorial view of a gas regulator 300, according to the prior art. Gas regulator 300 may include a flow meter 306, shown here, merely as an example, as a traditional Thorpe tube controlled by a rotating knob 304. However, other types of flow meters exist, such as electronic flow meters and others.

Gas is provided by gas regulator 300 through a nipple 302, which is often constructed as a male plug having a plurality of bulging rings 302a on its outer surface, for the purpose of enhancing the gas-tight seal between the nipple and the adapter mounted onto it.

Figure 4:
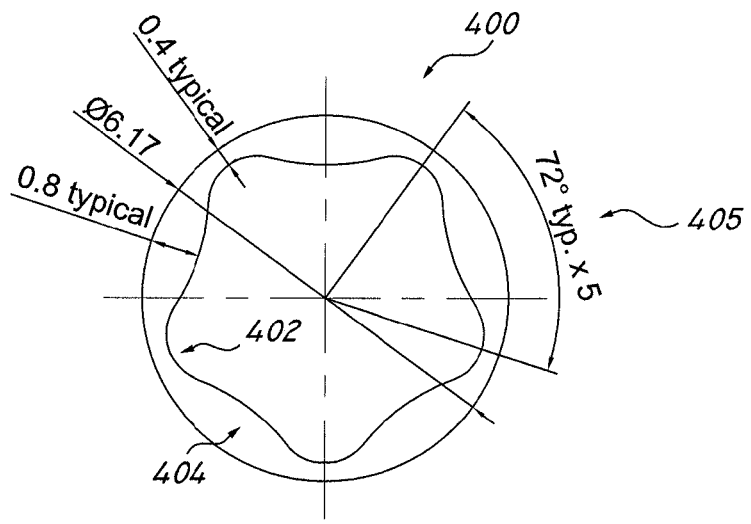
FIG. 4 shows a cross-sectional view of the tube geometry.

Reference is now made to FIG. 4, which shows a cross-sectional view of a kink-resistant gas delivery tube 400, according to an embodiment. Advantageously, tube 400 may be constructed in such a way that it may be both kink-resistant (optionally in compliance with one or more of the pertinent standards, such as those referenced in the background section above) and directly connectable to a circular nipple of a gas regulator (such as nipple 302 of FIG. 3), while forming an essentially gas-tight seal.

An additional advantage of tube 400 is its low resistance to flow (optionally in compliance with one or more of the previously-mentioned standards), resulting from its relaxed inner configuration and/or its relatively low inner surface area; again, this virtue of the tube is achieved, advantageously, while not significantly compromising its kink-resistibility and its direct connectivity to the gas regulator nipple.

In an embodiment, tube 400 may include a relaxed concave-convex configuration. Tube 400 may include, in its internal geometry, a plurality of concave areas (hereinafter "concavities") 402 and a plurality of convex areas (hereinafter "convexities") 404 arranged in a parabolic shape. As an example, five concavities 402 and five convexities 404 are shown, each concavity-convexity pair spreading over 72 degrees 405, but a different number of these features is explicitly intended herein.

Figure 5:
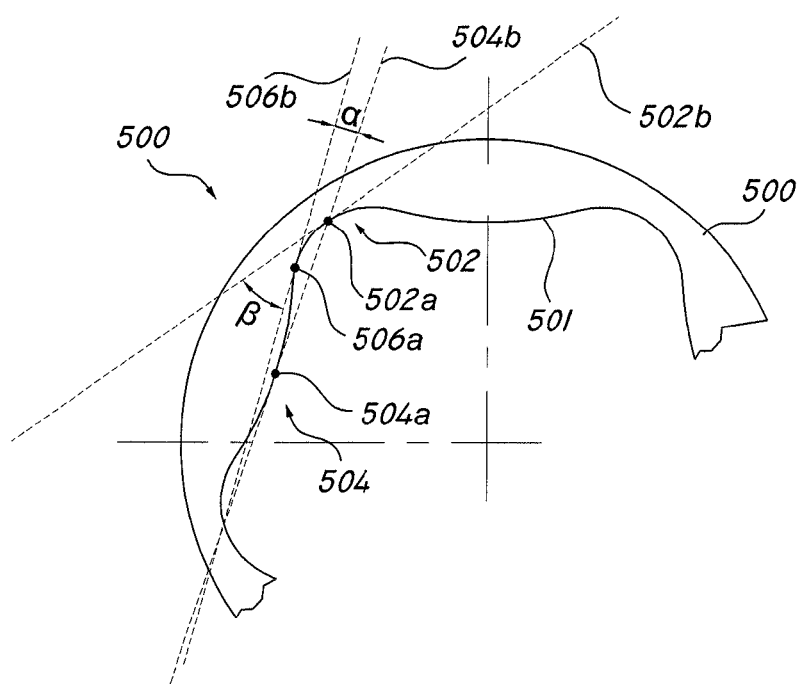
FIG. 5 shows an enlarged portion of the cross-sectional view of the tube geometry.

The relaxed concave-convex configuration may be expressed in one or more parameters:

A first parameter may be, for example, a relatively small angular difference between each of the apexes of concavities 402 and convexities 404, and the slope between these apexes. Reference is now made to FIG. 5, which shows an enlarged portion 500 of kink-resistant gas delivery tube 400 of FIG. 4, in which this first parameter is clearly visible. To illustrate this parameter, a number of definitions have to be initially made: An internal configuration 501 of tube 400 may be referred to as a parabola (or as a series of connected parabolic sections), where an apex 502a of a concavity 502 is a maximum point in a parabola, and apex 504a of convexity 504 is a minimum point in a parabola. A tangent line 502b to apex 502a and a tangent line 504b to apex 504b are shown. In between apexes 502a and 504a, the slope of the parabola constantly changes. A maximum slope point 506a of the parabola is where the value of the slope is maximal. A tangent line 506a to maximum slope point 506a is shown.

Advantageously, under these definitions, an angle α (alpha) between tangent line 504b and tangent line 506a is a sharp angle, shown here, by way of example, as an approximately 10 degree angle. In another embodiment (not shown), an angle α may be between approximately 5-15 degrees, while in yet another embodiment (not shown), an angle α may be between approximately 16-30 degrees.

Similarly, and also much advantageously, an angle β (beta) between tangent line 502b and tangent line 506a may be a sharp angle, shown here, by way of example, as an approximately 30 degree angle. In another embodiment (not shown), an angle β may be between approximately 5-15 degrees, while in yet another embodiment (not shown), an angle β may be between approximately 16-29 degrees.

Yet another advantage may be a ratio between angles α an β. In this figure, the ratio is approximately 1:3. In other embodiments (not shown), the ratio may be, for example, in the range of 1:1 to 1:4.5. It should be noted that the ratio is interchangeable, namely, it may be regarded as the ratio between α an β or between β and α.

It should be noted that in other embodiments (not shown), multiple, equal maximum slope points may exist, such as if multiple "waves" are present in the parabola between the maximum and minimum points. However, this need not change the specified, advantageous, angle ranges and ratio ranges.

A second parameter expressing the relaxed concave-convex configuration may be expressed by a relatively small difference in the wall thickness of the kink-resistant tube between the concavities and the concavities. Referring now back to FIG. 4, a ratio between the wall thickness at concavities 402 and the thickness at convexities 404 is approximately 1:2. In other embodiments (not shown), the thicknesses may be different, and the ratio between them may be in the range of 1:1.25 to 1:3.

In an embodiment, an advantageous feature of tube 400 is the material from of which it may be made, and/or the thickness of the material. A relatively elastic material, such as soft polyvinyl chloride (PVC), may be used for making tube 400. The PVC may be made soft by the addition of plasticizers during its manufacturing. The elasticity of tube 400 may enhance its ability to adapt to the circular shape of the nipple and create a gas-tight seal when manually pressed upon it. When pressure is applied on the internal structure of tube 400 by the circular nipple, this structure may stretch, pushing the areas of convexities 404 outside, so that an essentially circular internal shape of the tube is achieved, and an essentially gas-tight connection is formed.

Additionally or alternatively, the thickness of the walls of tube 400, both at concavities 402 and at convexities 404 may be relatively low (although not equal, naturally), so as to allow the tube to better adapt to the circular shape of the nipple when manually pressed upon it. In this exemplary embodiment, the thickness of the wall at concavities 402 is approximately 0.4 millimeters, while the thickness at convexities 404 is approximately 0.8 millimeters, thereby enhancing the ability of the walls to stretch, pushing the areas of convexities 404 outside, so that an essentially circular internal shape of the tube is achieved, and an essentially gas-tight connection is formed. It should be noted that a diameter of exemplary tube 400 is approximately 6 millimeters. In other embodiments (not shown), where the diameter is smaller or larger, the wall thicknesses may decrease or increase, respectively. In yet further embodiments (not shown), the walls of the tube may have a different thickness than what is shown in FIG. 4, such as a thickness in the range of 0.2 to 0.8 millimeters at the concavities and in the range of 0.4 to 1.6 millimeters at the convexities, respectively or irrespectively.

EXPERIMENTAL RESULTS

An experiment comparing the present kink-resistant gas delivery tube (such as tube 400 of FIG. 4) with six common prior art tubes has been performed. The experiment has been conducted in accordance with sections 5.1.1 and 5.1.5 of European Standard No. EN 13544-2:2002E, which define, inter alia: (1) the maximum flow restriction created by the respective tube internal geometry; and (2) the minimum acceptable flow when a restriction (kink) is created. The results are shown in the table below:

| Tube | (1) Resistance of tubing to gas flow (According to section 5.1.1 of the European standard) (in kPA/meter) Pass criteria max.: 0.9 kPa/meter | (2) Kink resistance of tubing (when tested According to section A6 of the European standard) (after 10 minutes, in Liters per minute, LPM) Pass criteria: 7.5LPM min. |
|---|---|---|
| Oxyplus OP-2000-8 | 0.41 | 8.5 LPM, 4 kPA |
| Salter 1600 TLC | 0.35 | 10 LPM, 5.3 kPA |
| OXYMASK | 0.41 | 9.5 LPM, 14.5 kPA |
| Capnoxygen CO2-04 | 0.45 | 9.5 LPM, 125 mBar 12.5 kPA |
| Airlite 001350 | 0.25 | 9.5 LPM, 9 kPA |
| Present tube | 0.11 | 10 LPM, 4.6 kPA |

As shown, the present tube passes both test criteria, while showing superior and remarkable performance in the flow resistance category. This may be explained by the direct correlation between the resistance to flow and the tube's internal surface area, due to friction between the gas and the tube's internal walls. The unique geometry of the present tube, with its relaxed concave-convex configuration, results in an internal surface area which is smaller than less relaxed configurations, where the stronger amplitudes are translated to an enlarged surface area. Therefore, the present tube may be especially advantageous in cases where the gas supply pressure is relatively low, since the tube will then allow much higher flow than tubes having less relaxed configurations.

While a number of exemplary aspects and embodiments have been discussed above, those of skill in the art will recognize certain modifications, permutations, additions and sub-combinations thereof. It is therefore intended that claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. A kink-resistant gas delivery tube configured to be directly connected to a circular male plug, the tube comprising an internal geometry of a parabola having multiple concave areas each having an apex representing a maximum point of the parabola and convex areas each having an apex representing a minimum point of the parabola,
   wherein an angle α between a tangent line to each of the apexes of the multiple concave areas and a tangent line to points of maximum slope of the parabola is 30 degrees or less, or
   wherein an angle β between a tangent line to each of the apexes of the multiple convex areas and a tangent line to points of maximum slope of the parabola is 30 degrees or less; and
   wherein said angle α and said angle β are configured to ensure that an essentially circular internal shape is achieved when pressure is applied on said internal geometry of said tube, such that a flow resistance of said tube is less than approximately 0.25 kPa/meter at a flow rate of 4 liters per minute.

2. The kink-resistant gas delivery tube according to claim 1, wherein angle α is in the range of approximately 5-15 degrees.

3. The kink-resistant gas delivery tube according to claim 1, wherein angle α is in the range of approximately 16-29 degrees.

4. The kink-resistant gas delivery tube according to claim 1, wherein angle β is in the range of approximately 5-15 degrees.

5. The kink-resistant gas delivery tube according to claim 1, wherein angle β is in the range of approximately 16-29 degrees.

6. The kink-resistant gas delivery tube according to claim 1, wherein a ratio between angle α and angle β is in the range of approximately 1:1 to 1:4.5.

7. The kink-resistant gas delivery tube according to claim 1, wherein a ratio between angle β and angle α is in the range of approximately 1:1 to 1:4.5.

8. The kink-resistant gas delivery tube of claim 1, wherein said tube is configured to be directly connected to a circular male plug, the tube comprising an internal geometry of multiple concave and convex areas, wherein a ratio between a wall thickness of said tube at a concave area and a at convex area is in the range of 1:1.25 to 1:3; wherein said ratio is configured to ensure that an essentially circular internal shape is achieved when pressure is applied on said internal geometry of said tube, such that a flow resistance of said tube is less than approximately 0.25 kPa/meter at a flow rate of 4 liters per minute.

9. The kink-resistant gas delivery tube according to claim 8, wherein said tube has an outer diameter of approximately 6 millimeters and a wall thickness of approximately 0.4 millimeters at a concave area and 0.8 millimeters at a convex area.

10. The kink-resistant gas delivery tube according to claim 1, wherein said tube is made of soft PVC, wherein said soft PVC is made by addition of plastizer.

11. The kink-resistant gas delivery tube according to claim 1, wherein less than approximately 0.25 kPa/meter at a flow rate of 4 liters per minute comprises approximately 0.11 kPa/meter at a flow rate of 4 liters per minute.

12. The kink-resistant gas delivery tube according to claim 1, wherein less than approximately 0.25 kPa/meter at a flow rate of 4 liters per minute comprises between approximately 0.07 and 0.15 kPa/meter at a flow rate of 4 liters per minute.

13. The kink-resistant gas delivery tube according to claim 1, wherein said tube, when kinked, enables a flow rate of approximately 7.5 liters per minute or more with a resistance less than 0.25 kPa/meter.

14. The kink-resistant gas delivery tube according to claim 13, wherein approximately 7.5 liters per minute or more comprises approximately 10 liters per minute or more.

* * * * *